United States Patent

US007332601B2

(12) United States Patent
Cai et al.

(10) Patent No.: US 7,332,601 B2
(45) Date of Patent: Feb. 19, 2008

(54) CCI-779 DERIVATIVES AND METHODS OF MAKING SAME

(75) Inventors: Ping Cai, New City, NY (US); Mark Ruppen, Garnerville, NY (US); Russ Tsao, Tenafly, NJ (US)

(73) Assignee: Wyeth, Madison, NJ (US)

( * ) Notice: Subject to any disclaimer, the term of this patent is extended or adjusted under 35 U.S.C. 154(b) by 252 days.

(21) Appl. No.: 11/200,383

(22) Filed: Aug. 9, 2005

(65) Prior Publication Data

US 2006/0036091 A1 Feb. 16, 2006

Related U.S. Application Data

(60) Provisional application No. 60/600,337, filed on Aug. 10, 2004.

(51) Int. Cl.
*C07D 498/22* (2006.01)
(52) U.S. Cl. ..................................................... 540/456
(58) Field of Classification Search ................ 540/456; 546/207
See application file for complete search history.

(56) References Cited

U.S. PATENT DOCUMENTS

| 4,316,885 | A | 2/1982 | Rakhit |
| 5,102,876 | A | 4/1992 | Caufield et al. |
| 5,256,790 | A | 10/1993 | Nelson et al. |
| 5,362,718 | A | 11/1994 | Skotnicki et al. |
| 6,277,983 | B1 | 8/2001 | Shaw et al. |
| 7,202,256 | B2 | 4/2007 | Gu et al. |
| 7,268,144 | B2 | 9/2007 | Gu et al. |
| 2005/0033046 | A1 | 2/2005 | Chew et al. |
| 2005/0234087 | A1 | 10/2005 | Gu et al. |
| 2005/0239178 | A1 | 10/2005 | Ruppen et al. |
| 2007/0105888 | A1 | 5/2007 | Gu et al. |
| 2007/0212371 | A1 | 9/2007 | Gu et al. |

FOREIGN PATENT DOCUMENTS

| WO | WO95/28406 A1 | 10/1995 |
| WO | WO01/23395 A2 | 4/2001 |
| WO | WO-2005/016935 A | 2/2005 |
| WO | WO2005/016935 A3 | 2/2005 |

OTHER PUBLICATIONS

J. Alexandre, et al., La rapamycine et le CCI-779 (Rapamycin and CCI-779), Bull. Cancer 1999, pp. 808-811, vol. 86, XP-001078856.
Sambrook et al, Molecular Cloning: A Laboratory Manual, 2nd edtion, Col Spring HJarbor Laboratory Press (1989).
Strausberg et al, Proc Natl. Acad Sci. 99(26):16899-903 (Dec. 24, 2002).
Galanis et al, Phase II of Temsirolimus (CCI-779) in recurrent Glioblastoma Multiforme: A North Central Cancer Treatment Group Study, Journal of Clinical Oncology, vol. 23, No. 23, (Aug. 10, 2005).
Luengo et al, Structure-Activity Studies of Rapamycin Analogs: Evidence that the C-7 Methoxy Group is Part of the Effector Domain and Positioned at the FKBP12-FRAP Interface, Chemistry & Biology, 2:471-481, (Jul. 1995).

*Primary Examiner*—Bruck Kifle
(74) *Attorney, Agent, or Firm*—Arnold S. Milowsky; Howson & Howson LLP

(57) ABSTRACT

A method of generating synthetic metabolites of CCI-779 is provided. Five novel CCI-779 derivatives are described, as are methods of using these derivatives for detecting CCI-779 metabolites in samples.

10 Claims, No Drawings

CCI-779 DERIVATIVES AND METHODS OF MAKING SAME

CROSS-REFERENCE TO RELATED APPLICATION

This application is a non-provisional application which claims the benefit under 35 USC 119(e) of U.S. Patent Application No. 60/600,337, filed Aug. 10, 2004.

BACKGROUND OF THE INVENTION

The invention provides novel derivatives of CCI-779 formed using a unique enzymatic process.

Rapamycin 42-ester with 2,2-bis(hydroxymethyl)propionic acid (CCI-779) is an ester derivative of rapamycin which has demonstrated significant inhibitory effects on tumor growth in both in vitro and in vivo models.

CCI-779 may delay the time to progression of tumors or time to tumor recurrence which is more typical of cytostatic rather than cytotoxic agents. CCI-779 is considered to have a mechanism of action that is similar to that of sirolimus. CCI-779 binds to and forms a complex with the cytoplasmic protein FKBP, which inhibits an enzyme, mTOR (mammalian target of rapamycin, also known as FKBP12-rapamycin associated protein [FRAP]). Inhibition of mTOR's kinase activity inhibits a variety of signal transduction pathways, including cytokine-stimulated cell proliferation, translation of mRNAs for several key proteins that regulate the G1 phase of the cell cycle, and IL-2-induced transcription, leading to inhibition of progression of the cell cycle from $G_1$ to S. The mechanism of action of CCI-779 that results in the $G_1$-S phase block is novel for an anticancer drug.

In vitro, CCI-779 has been shown to inhibit the growth of a number of histologically diverse tumor cells. Central nervous system (CNS) cancer, leukemia (T-cell), breast cancer, prostate cancer, and melanoma lines were among the most sensitive to CCI-779. The compound arrested cells in the $G_1$ phase of the cell cycle.

In vivo studies in nude mice have demonstrated that CCI-779 has activity against human tumor xenografts of diverse histological types. Gliomas were particularly sensitive to CCI-779 and the compound was active in an orthotopic glioma model in nude mice. Growth factor (platelet-derived)-induced stimulation of a human glioblastoma cell line in vitro was markedly suppressed by CCI-779. The growth of several human pancreatic tumors in nude mice as well as one of two breast cancer lines studied in vivo also was inhibited by CCI-779.

A great deal of effort has been put on the preparation of its new derivatives to explore the structure-activity. However, due to the presence of multiple functional groups, rapamycin is very susceptible to acidic and basic reaction conditions. Therefore, selective structural modification is difficult. Modification of rapamycin has mainly focused on the 42-hydroxy position as its ether and ester products (for example: CCI-779), and 7-position derivatives. Few products other than 7, and 42-position modifications have been reported.

SUMMARY OF INVENTION

The present invention provides a method of selectively generating CCI-779 reduction and hydroxylation derivatives using a CYP3A4 isozyme system. Using this system, five novel CCI-779 derivatives, which resulted from the selective $C_{27}$-ketone reduction, 36-hydroxylation, 35-hydroxylation, 11-hydroxylation, and N-oxidation of CCI-779, respectively, have been identified. Various uses for these methods and compositions of the invention are provided.

Other aspects and advantages of the invention will be apparent from the following detailed description of the invention.

DETAILED DESCRIPTION OF THE INVENTION

The CCI-779 compounds of the invention are believed to be synthetic equivalents to "metabolites" formed by processing CCI-779 by a subject, a mammal, a primate (non-human or human), or a human patient. Thus, the compounds of the invention are useful as standards used in monitoring CCI-779 therapy in a subject following administration of CCI-779 or a prodrug thereof, in the subject.

The invention provides a method of generating specific derivatives of CCI-779 by incubating CCI-779 with membranes of recombinant E. coli cells expressing human cytochrome P450-3A4 isozymes.

The preparation of and use of hydroxyesters of rapamycin, including CCI-779 is described in U.S. Pat. No. 5,362,718, which is hereby incorporated by reference. A regiospecific synthesis of CCI-779 is described in U.S. Pat. No. 6,277,983, which is hereby incorporated by reference. A regioselective synthesis of CCI-779 is described in U.S. Patent Publication No. US 2005/0033046 A1 (U.S. patent application Ser. No. 10/903,062), which is hereby incorporated by reference. CCI-779 is also available from commercial sources. The invention is not limited by the source of the CCI-779.

CCI-779 has the following structure:

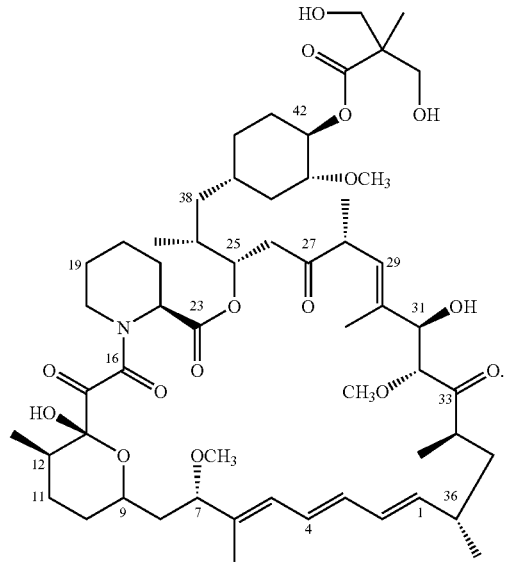

The CYP3A4 enzyme (human cytochrome P450, family 3, subfamily A, member 4), also known as human cytochrome P450-3A4, can be obtained commercially [e.g., BD Biosciences, 6 Henshaw St., Woburn, Mass. 01801 USA)]. Alternatively, the enzyme can be produced recombinantly. In one embodiment, the enzyme is produced in E. coli cells. However, other suitable host cells for expression of the enzyme can be any procaryotic or eukaryotic cells. Suitable methods for transfecting (or transforming) these host cells with a nucleic acid molecule encoding the enzyme can be found in Sambrook et al. (Molecular Cloning: A Laboratory Manual, 2nd Edition, Cold Spring Harbor Laboratory press (1989)), and other laboratory textbooks.

For example, a host cell transfected with a nucleic acid vector directing expression of a human CYP3A4 nucleotide sequence can be cultured under appropriate conditions to allow expression of the polypeptide to occur. A suitable nucleic acid sequence can be generated using the published sequences. See, e.g., Strausberg et al, *Proc Natl Acad Sci USA*, 99(26):16899-903 (Dec. 24, 2002) and GenBank, e.g., Accession No. BC 069418. Suitable media for cell culture are well known in the art. The CYP3A4 enzyme can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such polypeptides. In the case of membrane bound proteins, these can be isolated from a host cell by contacting a membrane-associated protein fraction with a detergent forming a solubilized complex, where the membrane-associated protein is no longer entirely embedded in the membrane fraction and is solubilized at least to an extent which allows it to be chromatographically isolated from the membrane fraction. Chromatographic techniques which can be used in the final purification step are known in the art and include hydrophobic interaction, lectin affinity, ion exchange, dye affinity and immunoaffinity.

Appropriate host cells include bacteria, archebacteria, fungi, especially yeast, and plant and animal cells, especially mammalian cells. Of particular interest are *C. albicans, E. coli, B. Subtilis, Saccharomyces cerevisiae, Saccharomyces carlsbergensis, Schizosaccharomyces pombi*, SF9 cells, C129 cells, 293 cells, Neurospora, CHO cells, COS cells, HeLa cells, and immortalized mammalian myeloid and lymphoid cell lines. Preferred replication systems include M13, ColE1, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced enzyme.

CYP3A4, a member of the human CYP450 family (also commercial available, such as BD Biosciences, Woburn, Mass. 01801), is the only member of this family of enzymes to specifically generate CCI-779 derivatives. Several other tested CYP450s, including 2A6, 2C8, 2C9, 2C19, and 2E1, are not able to generate these derivatives.

In order to generate the specific hydroxylation derivatives of the invention, CCI-779 and CYP3A4 may be incubated in the presence of a reducing agent, such as NADH or NADPH. Suitably, CCI-779 and the enzyme can be present in a ratio of 300:1 to 500:1, and desirably about 330:1 CCI-779 to enzyme. In the examples below, these components are mixed to a final concentration of 0.1 mM CCI-779, 300 nM 3A4 enzyme, and 2 mM NADPH regenerate system. However, other concentrations can be readily used.

In one embodiment, the reducing agent is NADPH. Optionally, a NADPH generating system is present, i.e., NADP, a phosphate source, a dehydrogenase, and a suitable buffering solution. A suitable dehydrogenase for use in this system can be readily selected from among known dehydrogenases, e.g., glucose-6-phosphate dehydrogenase, among others.

The NADPH regenerate system usually includes the NADP salt, D-glucose-6-phosphate, and glucose-6-phosphate dehydrogenase which reduces NADP to NADPH during incubation time, so the incubation solution is able to keep certain a amount of NADPH for the needs of the following reaction. Hydroxylation occurs via the general reaction: $RH+NADPH+O_2 \rightarrow ROH+NADP^++H_2O$, where RH is the substrate, i.e., CCI-779.

The resulting mixture solution is incubated and crude products are obtained by extraction with a suitable solvent. Optionally, incubation (i.e., the enzymatic reaction) is carried out at temperatures in the range of from 30° C. to about 40° C. Suitably, the pH is maintained in the range of about 6 to about 8, about 7 to about 8, or about 7.2 to about 7.6. Typically, the reaction time is from 30 minutes to 90 minutes. However, lower temperatures and longer incubation times may be used. Similarly, higher temperatures and shorter incubation times may be used, taking care to avoid destroying enzymatic activity prior to generation of the CCI-779 derivatives. In one embodiment, the mixture is incubated at about 37° C. for 1 hour. Suitably, the pH is maintained in the range of about 6 to about 9, about 7 to about 8, or 7.4.

In one embodiment, incubation is performed under oxygen atmosphere to maximize yield. Following incubation, the reaction solution is allowed to cool, and extracted to recover crude CCI-779 derivatives. Suitable extractants include, e.g., ethyl acetate and dichloromethane. Other extractants can be selected by one of skill in the art. Typically, the extracts are combined and evaporated under vacuum to get the crude products.

Conventional techniques can be used to recover the products from the incubation mixture. For example, the crude extract can be passed through a silica gel column and eluted with a gradient of solvents to remove unreacted CCI-779 and other material from reaction reagents. Suitable solvent for use in the gradients can be readily selected by one of skill in the art. In the example herein, hexane/acetone and acetone/methanol were used sequentially as the solvents. The fractions, which contain CCI-779 derivatives, are combined and the solvents were evaporated to provide the CCI-779 derivative mixture.

In order to isolate the individual derivatives, the purified mixture can be subjected to further separation using chromatographic techniques. For example, high performance liquid chromatography (HPLC) can be used. Suitable columns and conditions for separation will be readily apparent to one of skill in the art given the present disclosure.

Without wishing to be bound by theory, the derivatives of the invention are unique synthetic metabolites that are believed to be bioequivalents to the metabolites produced by a subject following administration of CCI-779. Thus, the derivatives of the invention are useful as standards in kits for monitoring CCI-779 therapy, and for generating antibodies specific for CCI-779 metabolites. Such antibodies are useful for monitoring and studying the effects of CCI-779 therapy.

The derivatives of this invention may contain one or more asymmetric centers and may thus give rise to optical isomers and diastereoisomers. While shown without respect to stereochemistry below, the present invention includes such optical isomers and diastereoisomers; as well as the racemic and resolved, enantiomerically pure R and S stereoisomers; as well as other mixtures of the R and S stereoisomers and pharmaceutically acceptable salts thereof. Five derivatives of the invention are shown as follows.
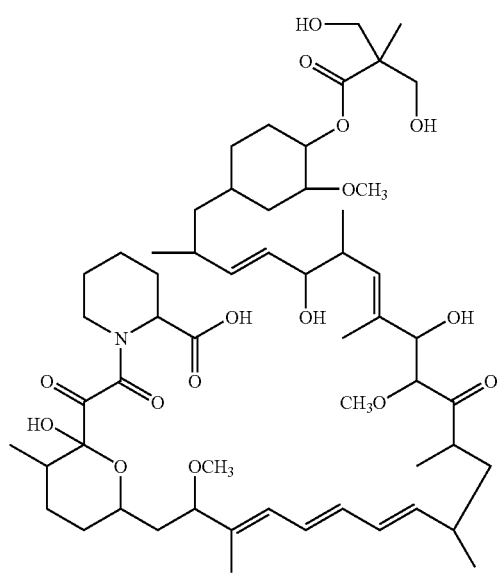
27-hydroxy seco-CCI-779 (M7)
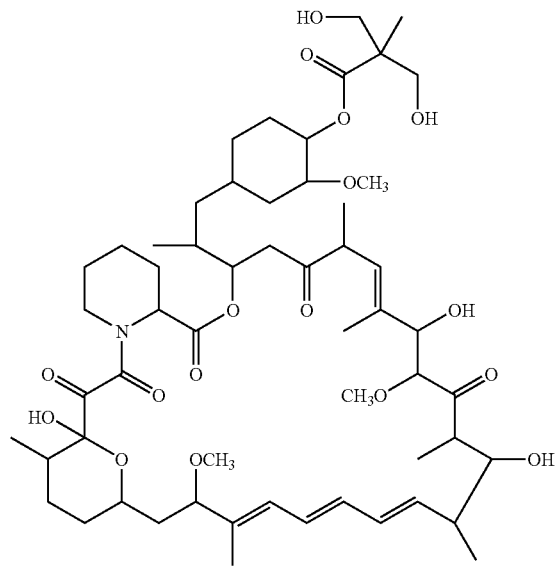
35-hydroxy CCI-779 (M9)
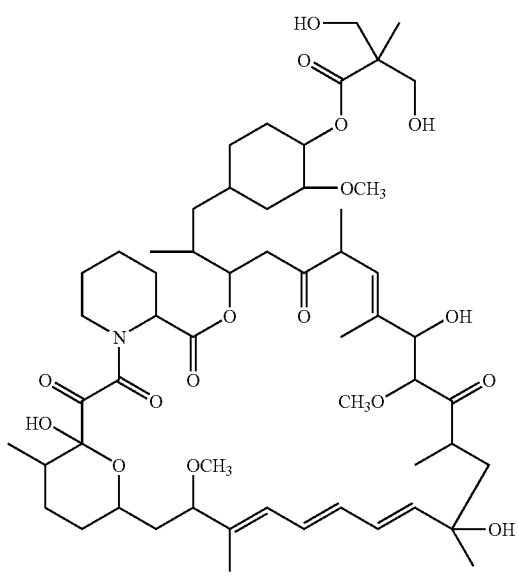
36-hydroxy CCI-779 (M8)
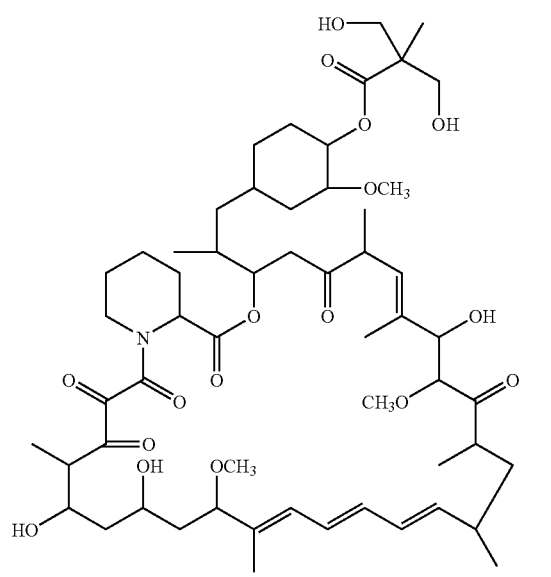
11-hydroxy CCI-779 (M10)

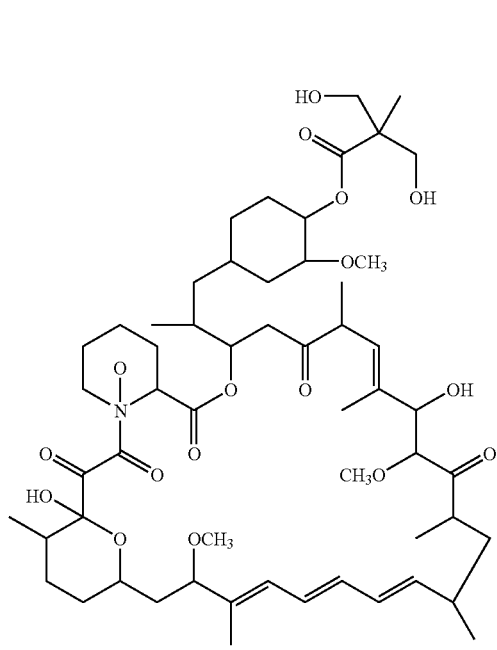
N-oxide CCI-779
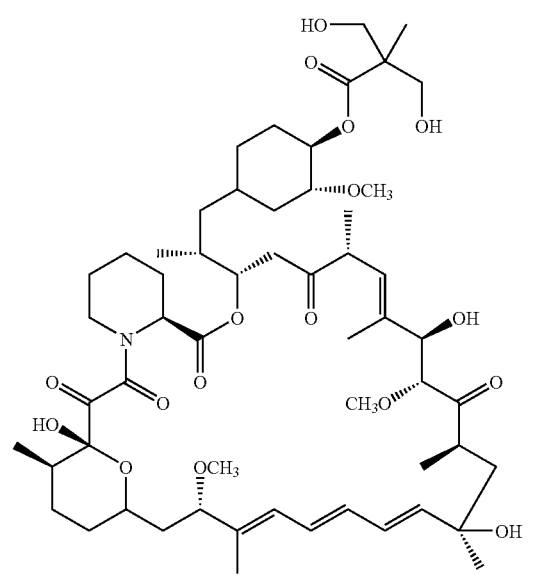
36-hydroxy CCI-779
In one embodiment, these compounds have the following stereochemistry.
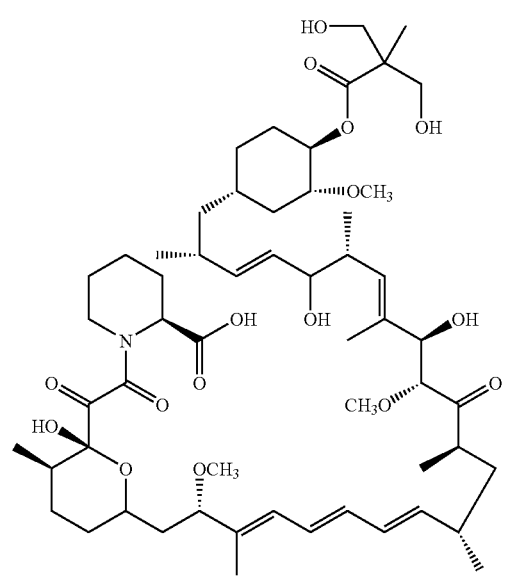
27-hydroxy seco-CCI-779
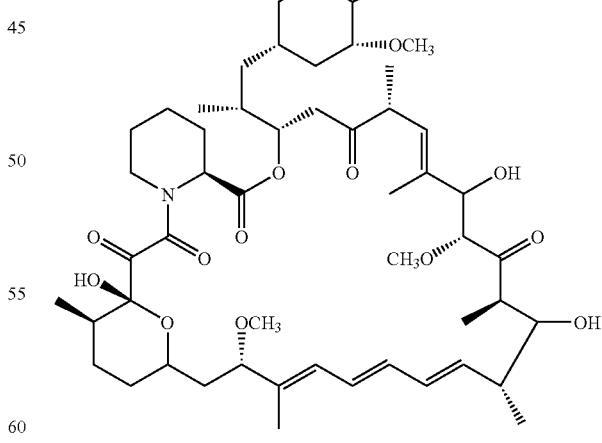
35-hydroxy CCI-779

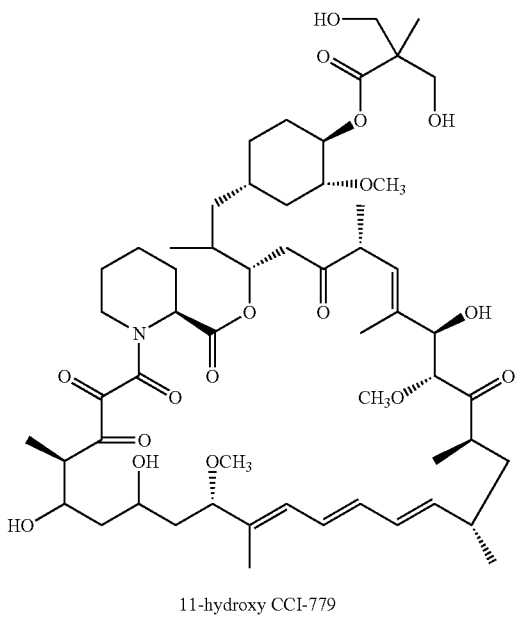

11-hydroxy CCI-779

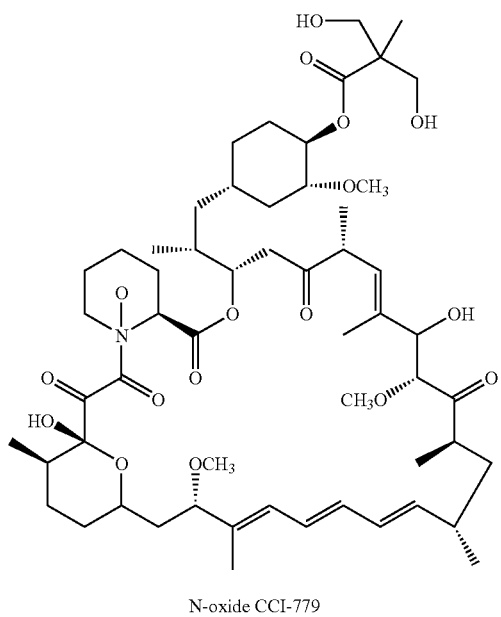

N-oxide CCI-779

In one embodiment, the invention further provides a composition containing a CCI-779 derivative of the invention. Such a composition can be used as a standard for a kit used to detect the presence of a CCI-779 metabolite in a sample.

A "sample" as used herein refers to a biological sample, such as, for example, tissue or fluid isolated from an individual, i.e., in vivo (including without limitation plasma, serum, cerebrospinal fluid, lymph, urine, saliva and tissue sections), or from in vitro cell culture constituents, as well as samples from the environment.

A kit of the invention may contain an appropriately labeled tracer, standard and instructions for use. The label for the tracer may be any suitable label, e.g., a radioactive, fluorescent or calorimetric label. Where convenient, the components of the kit may be in lyophilized form.

In one embodiment, the present invention provides monoclonal or polyclonal antibodies that bind to a CCI-779 derivative of the invention. In one embodiment, such an antibody selectively binds to the CCI-779 derivative of the invention, and distinguishes from CCI-779 and other metabolites thereof.

The term "antibody" as used herein is intended to include fragments thereof which are specifically reactive with CCI-779 and/or its metabolites.

An antibody specific to a CCI-779 derivative of the invention, e.g., M7, M8, M9, M10, or M11, is prepared using standard techniques wherein the antigen is a derivative of the invention. See, e.g., Sambrook, Molecular Cloning: A Laboratory Manual, Cold Spring Harbor Press, Cold Spring Harbor, N.Y.

The polyclonal and monoclonal antibodies to specific sites of a CCI-779 metabolite may be used for development of immunoassays or TDM (therapeutic drug monitoring) kits. Such assays could include, but are not limited to, direct, inhibition, competitive or sandwich immunoassays (ELISA or other assay systems), RIA (radioimmunoassays), solid or liquid phase assays or automated assay systems.

Where a competitive assay is used, the competitor for the antibody may be a CCI-779 derivative of the invention bound to the assay plate, or a labeled derivative, e.g., a fluorolabeled derivative, a radiolabeled derivative, or a tritiated derivative.

The assay procedure of the invention has the advantages that it may be carried out rapidly and simply using standard bioanalytical equipment to give accurate and reproducible results. Also, whole blood may be used without the need for extraction.

The invention also provides an assay kit suitable for detecting the amount of CCI-779 metabolite in blood the kit comprising a binding competitor that displaces the pharmaceutical from CCI-779 metabolite in the blood; and an antibody that binds to the pharmaceutical but not significantly to the binding competitor.

EXAMPLES

The following examples are illustrative of the methods for generating derivatives of the invention.

Example 1

Preparation of CCI-779 Derivatives

To a 5L reactor containing CCI-779 514 mg (0.5 mmol), $MgCl_2$ (0.4 M×100 ml), NADPH generating system (NADP sodium salt: 75 mg×100 mL, D-glucose-6-phospate: 60 mg/mL×100 mL; glucose-6-phosphate dehydrogenase: 25 units/mL×100 mL), and E. coli-expressed CYP-3A4 membrane (1500 nmol) was added potassium phosphate buffer solution to 5L. The mixture solution was incubated at 37° C. under oxygen atmosphere (sparging $O_2$ at 0.3 L/min) with agitation of 125 rpm for one hour. After one-hour reaction, the reaction solution was cooled down to 25° C. on an ice bath and extracted with an equal volume of ethyl acetate twice. The ethyl acetate extracts were combined and evaporated under vacuum to get the crude incubation extracts (~500 mg).

Example 2

Isolation and Purification of the Crude Extract

The crude extract was passed through a flash silica gel column to get rid of unreacted CCI-779 and the other materials from the reaction reagents. A gradient of hexane/acetone and acetone/methanol was used as the solvent. The fractions, which contained CCI-779 derivatives, were combined. After solvents were evaporated, the CCI-779 derivative mixture was obtained and subjected to further separation by semi-preparative HPLC. The semi-preparative HPLC was accomplished on a Supelcosil™ LC-18 column and a gradient of water containing 5 mM ammonium acetate/methanol (from 4:6 to 2:8 in 90 min at a flow rate of 2 mL/min) was used as the mobile phase. The isolation was monitored by UV detector setting at 220 and 280 nm, respectively. Each CCI-779 derivative peak was collected into the container on the ice bath. After solvents were evaporated under vacuum, thirteen pure derivatives were obtained.

Example 3

Structure Identification of Isolated Derivatives

The structures of the purified CCI-779 derivatives were determined by LC-MS, MS/MS, and MS/MS/MS spectral analysis as compared with those of CCI-779, which were further confirmed by high-resolution accurate mass measurement as well as $^1$H-NMR analysis. Among them, five novel compounds were identified, which were assigned as 27-hydroxy seco-CCI-779 (M7), 36-hydroxy CCI-779 (M8), 35-hydroxy CCI-779 (M9), 11-hydroxy CCI-779 (M10) and N-oxide CCI-779 (M12), respectively. Their structural formulas are as follows, wherein indicates the position of modification relative to CCI-779.

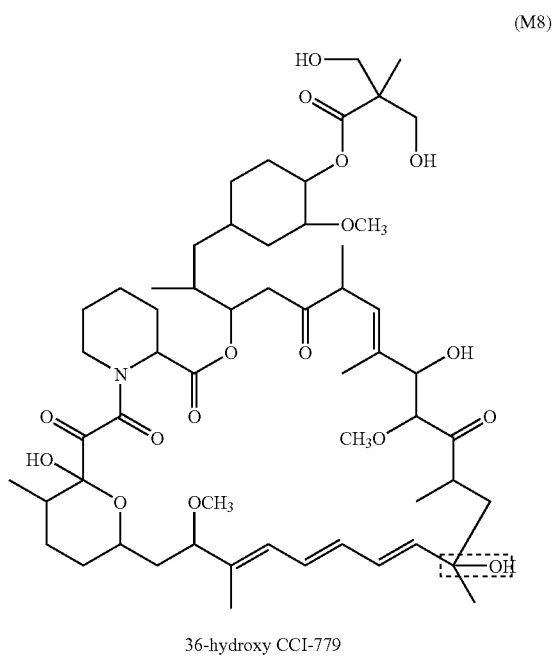

(M8)

36-hydroxy CCI-779

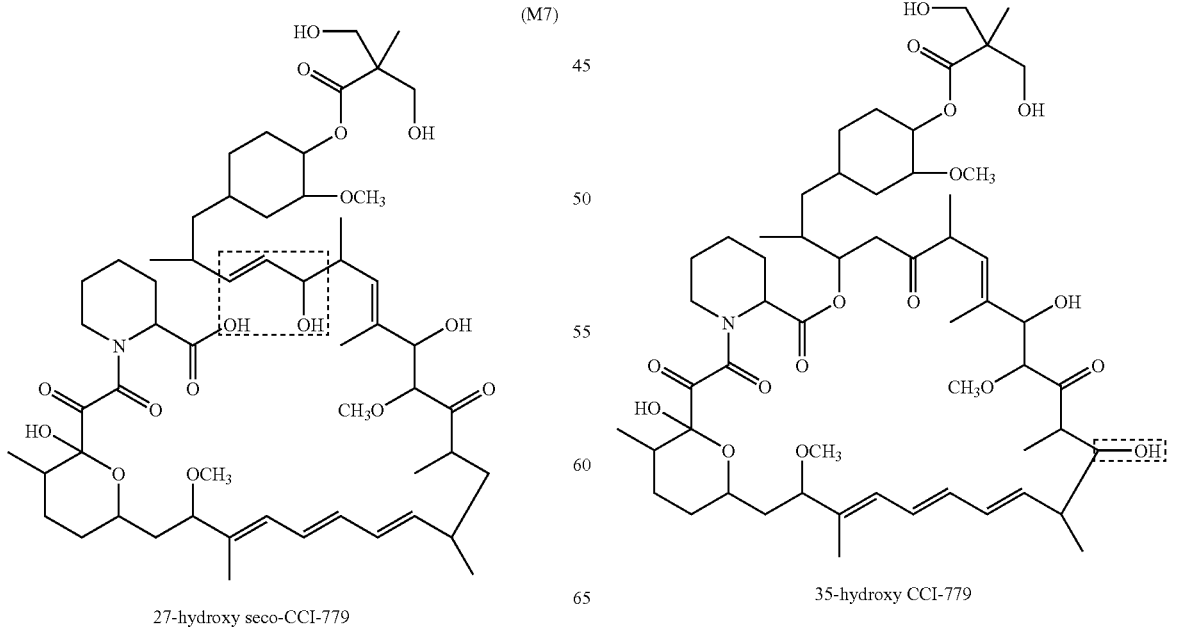

(M7) 27-hydroxy seco-CCI-779

(M9) 35-hydroxy CCI-779

-continued

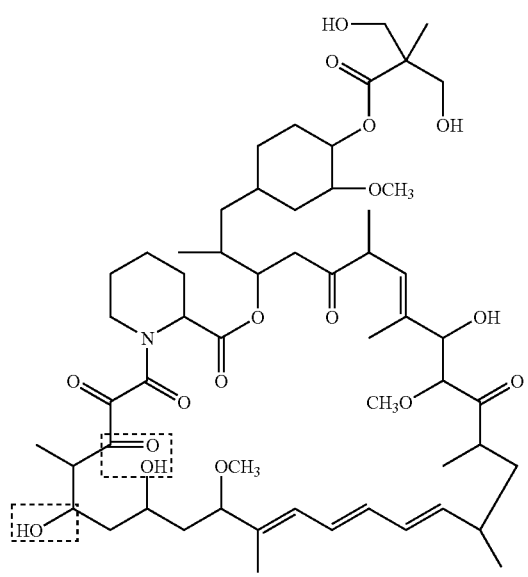

11-hydroxy CCI-779

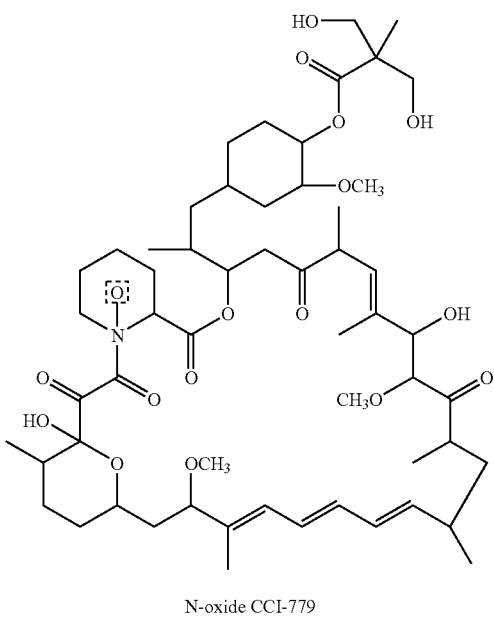

N-oxide CCI-779

All patents, patent publications, and other publications listed in this specification, are incorporated herein by reference. While the invention has been described with reference to particular embodiments, it will be appreciated that modifications can be made without departing from the spirit of the invention. Such modifications are intended to fall within the scope of the appended claims.

The invention claimed is:

1. A compound 27-hydroxy seco-CCI-779 (M7).
2. The compound according to claim 1 characterized by the structure:

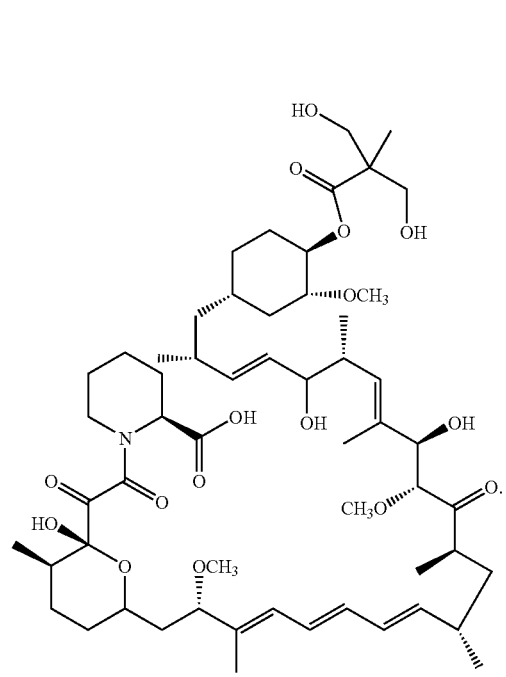

3. A compound 36-hydroxy CCI-779 (M8).
4. The compound according to claim 3 characterized by the structure:

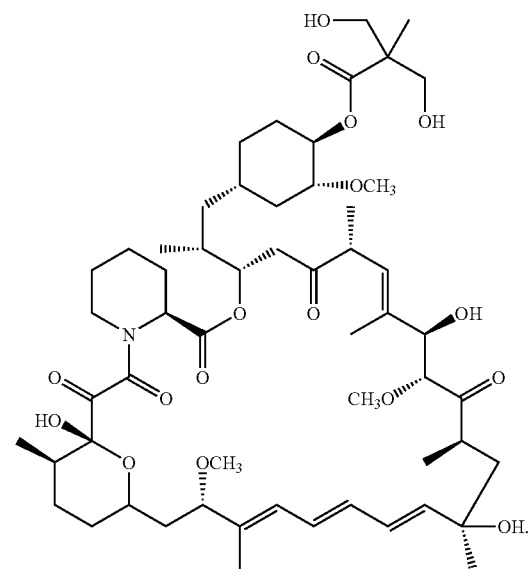

5. A compound 35-hydroxy CCI-779 (M9).

6. The compound according to claim 5 characterized by the structure:
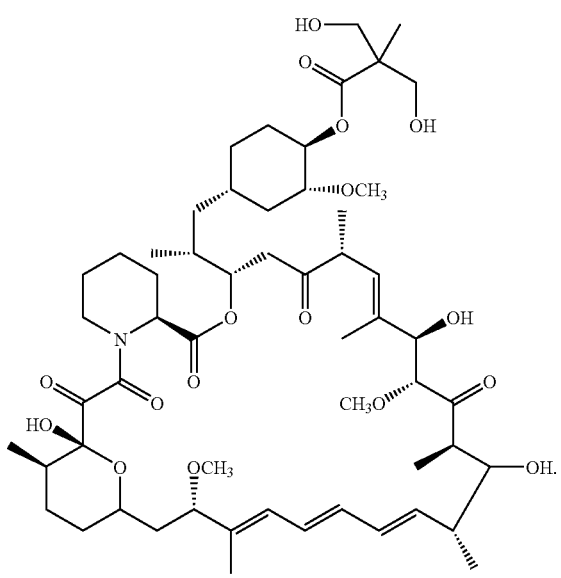
7. A compound 11-hydroxy CCI-779 (M10).
8. The compound according to claim 7 characterized by the structure:
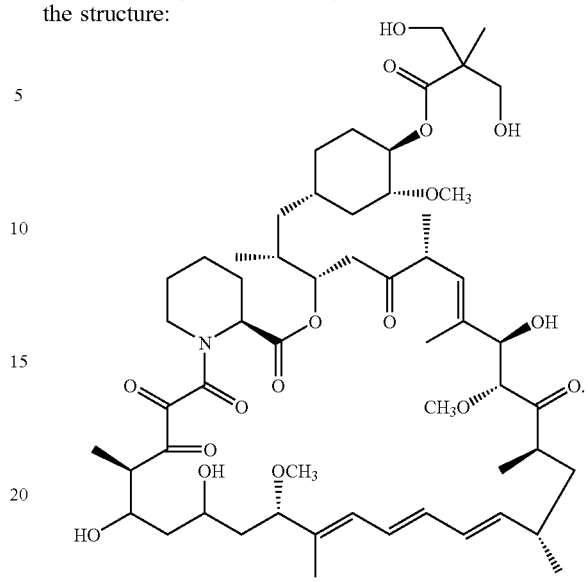
9. A compound N-oxide CCI-779 (M12).
10. The compound according to claim 9 characterized by the structure:
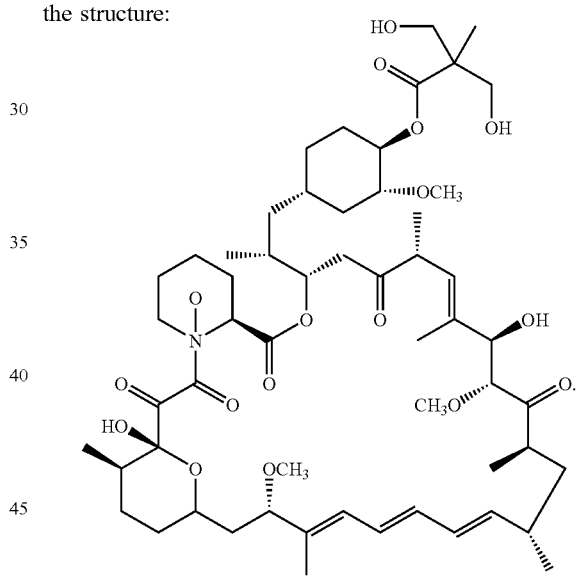
* * * * *